(12) United States Patent
Uckun et al.

(10) Patent No.: US 6,545,152 B1
(45) Date of Patent: Apr. 8, 2003

(54) R-ISOMERS OF NONNUCLEOSIDE INHIBITORS

(75) Inventors: Fatih M. Uckun, White Bear Lake, MN (US); Taracad K. Venkatachalam, St. Anthony, MN (US)

(73) Assignee: Parker Hughes Institute, Roseville, MN (US)

( * ) Notice: Subject to any disclaimer, the term of this patent is extended or adjusted under 35 U.S.C. 154(b) by 0 days.

(21) Appl. No.: 09/619,130

(22) Filed: Jul. 18, 2000

(51) Int. Cl.[7] .................. C07D 265/30; C07D 295/08; C07D 211/06; C07D 307/02; C07C 335/08

(52) U.S. Cl. .................. 544/106; 544/159; 544/162; 544/170; 544/224; 544/238; 544/322; 544/358; 544/382; 546/192; 546/205; 546/208; 546/216; 548/196; 548/214; 548/251; 548/253; 548/330.1; 548/330.5; 548/469; 548/483; 549/29; 549/69; 549/480; 564/17; 564/32; 564/48

(58) Field of Search .................. 514/235.5, 252, 514/316; 544/124, 360, 106, 159, 162, 170, 224, 238, 322, 358, 382; 546/208, 192, 205, 216; 564/17, 32, 48; 549/29, 69, 480; 548/196, 214, 251, 253, 330.1, 330.5, 469, 483

(56) References Cited

U.S. PATENT DOCUMENTS

| | | | | |
|---|---|---|---|---|
| 5,593,993 A | * | 1/1997 | Morin et al. | 14/247 |
| 5,658,907 A | | 8/1997 | Morin, Jr. et al. | 514/247 |
| 5,686,428 A | | 11/1997 | Eriksson et al. | 53/441 |
| 5,714,503 A | | 2/1998 | Morin, Jr. et al. | 514/332 |
| 5,786,462 A | | 7/1998 | Schneider et al. | 536/23.1 |
| 5,998,411 A | * | 12/1999 | Vig et al. | 514/235.5 |

FOREIGN PATENT DOCUMENTS

| | | | |
|---|---|---|---|
| EP | 0 420 763 A2 | 4/1991 | 514/252 |
| EP | 0 540 143 A2 | 5/1993 | 514/252 |
| JP | WO 93/03022 | 2/1993 | 514/252 |
| JP | 07025770 | 1/1995 | 514/252 |
| WO | WO 95/06034 | 3/1995 | 514/235.5 |
| WO | WO 99/29318 | 6/1999 | 514/235.8 |
| WO | WO 99/47501 | 9/1999 | |

OTHER PUBLICATIONS

Bosworth, N et al., "Scintillation Proximity Assay", *Nature International Weekly Journal of Science*, vol. 341, No. 6238, pp. 167–168 (Sep. 14, 1989).

Burkett, U. et al., "Methods For The Computation Of Molecular Geometry", *Molecular Mechanics, ACS Monograph 177*, pp. 59–78 (1982 American Chemical Society).

Erice, A. et al., "Anti–Human Immunodeficiency Virus Type 1 Activity Of An Anti–CD4 Immunoconjugate Containing Pokeweed Antiviral Protein", *Antimicrobial Agents & Chemotherapy*, vol. 37, No. 4, pp. 835–838 (Apr. 1993).

Kohlstaedt, L. et al., "Crystal Structure At 3.5 Å Resolution Of HIV–1 Reverse Transcriptase Complexed With An Inhibitor", *Science*, Vo. 256, pp. 1783–1790 (Jun. 26, 1992).

Marshall, G., "Computer–Aided Drug Design", *Annual Review of Pharmacology And Toxicology*, vol. 27, pp. 193–213 (1987).

Remington's Pharmaceutical Sciences, RPS XIV, Chapter 43, pp. 764–786 (Date Unknown).

Uckun, F. et al., "TXU (Anti–CD7)–Pokeweed Antiviral Protein As a Potent Inhibitor Of Human Immunodeficiency Virus" *Antimicrobial Agents & Chemotherapy*, vol. 42, No. 2, pp. 383–388 (Feb. 1998).

Zarling, J. et al., "Inhibition of HIV Replication By Pokeweed Antiviral Protein Targeted To $CD4^+$Cells By Monoclonal Antibodies", *Nature International Weekly Journal Of Science*, vol. 347, No. 6288, pp. 92–95 (Sep. 6, 1990).

Ambinter: Exploratory Library, *Database Chemcats 'Online!*, Abstract XP–002184046 (May 31, 2001).

Ambinter: Exploratory Library, *Database Chemcats 'Online!*, Abstract XP–002184047 (May 31, 2001).

Breuzard, J.A.J. et al., "Thioureas as new chiral ligands for the asymmetric hydroformylation of styrene with rhodium(I) catalysts", *J. Mol. Catal. A: Chem*, 156(1–2), 223–232 (2000) Abstract.

Drefahl et al., "Stilbenes—(XXXIX) Wittig reaction with p–halomethylbenzaldehyde", *Database Caold 'Online!*, Abstract XP–002184037 (date unknown).

Furdik et al., Synergists of pyrethrum—(VI) synthesis of endo–cis–N–substituted 7–diphenylmethylene–bicyclo[1,2,2]hept–5–ene–2,3–dicarboximides, *Database Caold 'Online!*, Abstract XP–002184038 (date unknown).

Glover, Edward E., et al., "Synthesis and quaternization of heterocyclic mono–and disulfides", *J. Chem. Soc., Perkin Trans.* 1 (21) 2595–9 (1973) Abstract XP–002184040.

Iliceto, A., et al., "Thiocyanates and isothiocyanates—(III) kinetics and mechanism of benzhydryl thiocyanates isomerization",*Database Caold 'Online!*, Abstract XP–002184036 (date unknown).

Jung et al., "A study on the stability of 5,5–diamino–substituted–1,4,2–oxathiazoline derivatives", *Synth. Commun.* 28(10), 1879–1884 Abstract XP–002184044 (1998).

(List continued on next page.)

Primary Examiner—Alan L. Rotman
Assistant Examiner—Raymond Covington
(74) Attorney, Agent, or Firm—Merchant & Gould P.C.

(57) ABSTRACT

Novel chiral derivitaves of non-nucleoside inhibitors (NNI), particularly R-isomers of halopyridyl and thiazoyl thiourea compounds are provided as potent inhibitors of reverse transcriptase (RT), and particularly of retroviral RT, most particularly HIV RT. The stereospecific compounds and compositions of the invention inhibit replication of retrovirus, particularly human immunodeficiency virus-1 (HIV-1) and drug resistant strains.

19 Claims, 4 Drawing Sheets

OTHER PUBLICATIONS

Mao, et al., "Rational design of N–[2–(2,5–dimethoxyphenylethyl)]–N'–[2–(5–bromopyridyl)]–thioureaa (HI–236) as a potent non–nucleoside inhibitor of drug–resistant human immunodeficiency virus" *Bioorg. Med. Chem. Lett. 9*, 1593–1598, (1999).

Nagai et al., "Bisarylthiourea fungicides", *Japan, Kokai*, 6 pp. Abstract XP–002184043 (Feb. 3, 1978).

Patel, P.R., et al., "Synthesis of 5–alkyl–3–benzyhydryl–2–arylimino–4–thiazolidones and 5–substituted benzal/cinnamal–3–benzhydryl–2–arylimino–4–thiazolidones", *J. Inst. Chem.*, Calcutta 48, Pt. 2, 105–8, Abstract XP–002184041 (1976).

Sato et al., "Arylthioureas as microbicides", *Japan, Kokai*, 5 pp., Abstract XP–002184042 (Dec. 18, 1976).

Tonellato, U., et al., "Stereochemistry of ion–pair return. I. Resolution and isomerization of (–)–4–chlorobenzhydryl thiocyanate" *J. Org. Chem.*, 34(12), 4032–4, (1969).

Vig, R. et al., 1998 *Bioorganic & Medicinal Chemistry*, 6:1789–1797 Rational Design and Synthesis of Phenethyl–5–bromopyridyl Thiourea Derivatives as Potent Non–nucleoside Inhibitors of HIV Reverse Transcriptase.

Weiner, S.J. et al., 1984, *J. Am. Chem. Soc., 106*, 765–784 A New Force Field for Molecular Mechanical Simulation of Nucleic Acids and Proteins.

Zhang, et al., 1996, *Antiviral Chemistry & Chemotherapy*, 7(5):221–229 "Synergistic inhibition of HIV–1 reverse transcriptase and HIV–1 replication by combining trovirdine with AZT, ddI and ddC in vitro".

Ahgren, C., et al., 1995, *Antimicrob. Agents Chemotherapy*, 39, 1329–1335 The PETT Series, a New Class of Potent Nonnucleoside Inhibitors of Human Immunodeficiency Virus Type 1 Reverse Transcriptase.

Baba, M., et al., 1992, *Antiviral Res., 17*, 245–264 Highly potent and selective inhibition of HIV–1 replication by 6–phenylthiouracil derivatives.

Balzarini, J. et al., 1992, *Proc. Natl. Acad. Sci. U S A, 89*, 4392–4396 2',5'–Bis–O–(tert–butyldimethylsilyl)–3'–spiro–5"–(4"–amino–1",2"–oxathiole–2",2"–dioxide)pyrimidine (TSAO) nucleoside analogues: Hightly selective inhibitors of human immunodeficiency virus type 1 that are targeted at the viral reverse transcriptase.

Bartlett. P.A. et al., 1989, *Molecular Recognition in Chemical and Biological Problems, Special Pub., Royal Chem. Soc., 78*, 182–196 Caveat: A Program to Facilitate the Structure–derived Design of Biologically Active Molecules.

Bell, F. W., et al., 1995, *J. Med. Chem., 38*, 4929–4936 Penethylthiazolethiourea (PETT) Compounds, a New Class of HIV–1 Reverse Transcriptase Inhibitors. 1. Syntheis and Basic Structure–Activity Relationship Studies of PETT Analogs.

Blaney, J.M. and Dixon, J.S., 1993, *Perspectives in Drug Discovery and Design, 1,* 301 A good ligand is hard to find: Automated docking methods.

Bohm, H.J., 1992, *J. Comput. Aided. Mol. Des., 6,* 593–606 LUDI: rule–based automatic design of new substituents for enzyme inhibitor leads.

Bohm, H.J., 1992, *J. Comp. Aid. Molec. Design, 6,* 61–78 The computer program LUDI: A new mehtod for the de novo design of enzyme inhibitors.

Bohm, H. J., *J. Comput. Aided. Mol. Des., 1994,* 8, 243–256, 1996. The development of a simple empirical scoring function to estimate the binding constant for a protein–ligand complex of konwn three–dimensional structure.

Brooks, B.R. et al., 1983, *J. Comp. Chem., 4,* 187–217 CHARMM: A Program for Macromolecular Energy, Minimization, and Dynamics Calculations.

Cantrell A., et al., 1996, *J. Med. Chem., 39,* 4261–4274 Phenethylthiazolylthiourea (PETT) Compounds as a New Class of HIV–1 Reverse Transcriptase Inhibitors. 2. Synthesis and Further Structure–Activity Relationship Studies of PETT Analogs.

Chemical substance index page, *Chemical Abstracts, 13th Collective Chemical Substance Index,* Book 52, p. 1272 (1992–1996).

Connolly, M. L., 1983, *Science,* 221, 709–713 Solvent–Accessible Surfaces of Proteins and Nucleic Acids.

Danel, K., et al., 1996, *J. Med. Chem., 39,* 2427–2431 Synthesis and Potent Anti–HIV–1 Activity of Novel 6–Benzyluracil Analogues of 1–[2–Hydroxyethoxy)methyl]–6–(phenylthio)thymine.

Danel, K. et al., 1997 *Acta Chemica Scandinavica 51,* 426–430 Anti–HIV Active Napthyl Analogues of HEPT and DABO.

Danel, K. et al., 1998, *J. Med. Chem., 41,* 191–198 Synthesis and Anti–HIV–1 Activity of Novel 2,3–Dihydro–7H–thiazolo[3,2–α]pyrimidin–7–ones.

Zarling, et al., *Nature,* 1990, 347, 92–95.

Das, K. et al., 1996, *J. Mol. Biol., 264,* 1085–1100 Crystal Structures of 8–Cl and 9–Cl TIBO Complexed with Wild–type HIV–1 RT and 8–Cl TIBO Complexed with the Tyr181Cys HIV–1 RT Drug–resistant Mutant.

Davies et al., "Condensed Thiophen Ring Systems. Part XIX. Synthesis of 6,7–Dihydrothieno [3,2–c] pyridines and 4,5–Dihydrothieno [2,3–c] pyridines by Intramolecular Cyclisation of 2–(2– or 3–Thienyl)ethyl Isothiocyanate", *J.C.S. Perkin I,* pp. 138–141 (1976).

D–Cruz, O. et al., "Novel Thiourea Compounds As Dual–Function Microbicides", *Chemical Abstract,* Abstract No. 133:159648d, vol. 133, No. 12, 1 page (2000).

De Clercq, E., 1992, *J. Acquired Immune Defic. Syndr. Res. Human. Retrovirus, 8,* 119–134.

Ding, J., 1995, et al., *Nat. Struct. Biol., 2,* 407–415 Structure of HIV–RT/TIBO R 86183 complex reveals similarity in the binding of diverse nonnucleoside inhibitors.

Gittos et al., "A New Synthesis of Isocyanates", *J.C.S. Perkin I,* pp. 141–143 (1976).

Goodsell, D.S. and Olson, A.J., 1990, *Proteins: Struct. Funct. Genet., 8,* 195–202 The Molecular Biology of Human Immunodeficiency Virus Type 1 Infection.

Greene, W. C., 1991, *New England Journal of Medicine, 324,* 308–317 Automated Docking of Substrates to Proteins by Simulated Annealing.

Hopkins, A. L. et al., 1996, *J. Med. Chem., 39,* 1589–1600 Complexes of HIV–1 Reverse Transcriptase with Inhibitors of the HEPT Series Reveal Conformational Changes Relevant to the Design of Potent Non–Nucleoside Inhibitors.

Jones, T. A. et al., 1991, *Acta Crystallogr. A., 47,* 110–119 Improved Methods for Building Protein Models in Electron Denisty Maps and the Location of Errors in these Models.

Kuntz, I.D., et al., 1995, *J. Mol. Biol.,* 1982, 161, 269–288 A Geometric Approach to Macromolecule–Ligand Interactions.

Luty, B. A. et al., 1995, *J. Comp. Chem., 16,* 454–464 A Molecular Mechanics/Grid Methods for Evaluation of Ligand–Receptor Interactions.

Mai, A. et al., 1997, *J. Med. Chem., 40,* 1447–1454 Dihydro(alkylthio)(naphthylmethyl)oxopyrimidines: Novel Non– Nucleoside Reverse Transcriptase Indhibitors of the S–DABO Series.

Mao, C. et al., "Structure–Based Design of N–[2–(1–Piperidinylethyl)]–N'–[2–(5–Bromopyridyl)]–Thiourea and N–2–(1–Piperazinylethyl)–N'–[2–(5–Bromopyridyl)]–Thiourea as Potent Non–Nucleoside Inhibitors of HIV–1 Reverse Transcriptase", *Bioorganic & Medicinal Chemistry Letters 8,* pp. 2213–2218 (1998).

Mao, C. et al., "Rational Design Of N–[2–2,5–Dimethoxyphenylethyl)]–N'–[2–(5–Bromopyridyl)]–Thiourea (HI–236) As A Potent Non–Nucleoside Inhibitor Of Drug–Resistant Human Immunodeficiency Virus", *Bioorganic & Medicinal Chemistry Letters,* vol. 9, pp. 1593–1598 (1999).

Martin, Y.C., 1992, *J. Med. Chem., 35,* 2145–2154 3D Database Searching in Drug Design.

Mitsuya, H. et al., 1990, *Science, 249,* 1533–1544 Molecular Targets for AIDS Therapy.

Nishibata, Y. and Itai, A., 1991, *Tetrahedron, 47,* 8985 Automatic Creation of Drug Candidate Structures Based on Receptor Structure. Starting Point for Artificial Lead Generation.

Pauwel, R. et al., 1990, *Nature, 343,* 470–474 Potent and selective inhibitionof HIV–1 replication in vitro by a novel series of TIBO derivatives.

Pontikis, R. et al., 1997, *J. Med. Chem., 40,* 1845–1854 Synthesis and Anti–HIV Activity of Novel N–1 Side Chain–Modified Analogs of 1–[(2–Hydroxyethoxy)methyl]–6–(phenylthio)thymine (HEPT).

Ren, J. et al., 1995, *Structure, 3,* 915–926 The structure of HIV–1 reverse transcriptase complexed with 9–chloro–TIBO: lessons for inhibitor design.

Romero, D. L. et al., 1993, *J. Med. Chem., 36,* 1505–1508 Bis)heteroaryl)piperazine (BHAP) Reverse Transcriptase Inhibitors: Structure–Activity Relationships of Novel Substituted Indole Analogues and the Identification of 1–[(5–Methanesulfonamido–1H–indol–2–yl)–carbonyl]–4–[3–[(1–methylethyl)–amino]–pyridinyl]piperazine Monomethanesulfonate (U–90152S), a Second–Generation Clinical Candidate.

Sahlberg, et al., 1998, *Bioorganic & Medicinal Chemistry Letters 8,* pp. 1511–1516 "Synthesis and Anti–Hiv Activities of Urea–PETT Analogs Belonging to a New Class of Potent Non–Nucleoside HIV–1 Reverse Transcriptase Inhibitors".

Sudbeck, E. A. et al., 1998, *Antimicrobial Agents and Chemotherapy,* 42(12), 3225–33 Structure–Based Design of Novel Dihydroalkoxybenzyloxopyrimidine Derivatives as Potent Nonnucleoside Inhibitors of the Human Immunodeficiency Virus Reverse Transcriptase.

Tanaka, H. et al., 1991, *J. Med. Chem., 34,* 349–357 A New Class of HIV–1–Specific 6–Substituted Acyclouridine Derivatives: Synthesis and Anti–HIV–1 Activity of 5– or 6–Substituted Analogues of 1–[(2–Hydroxyethoxy)methyl]– 6–(phenylthio)thymine (HEPT).

Tanaka, H. et al., "Synthesis of a Potential Photoaffinity Labeling Reagent for HIV–1 Reverse Transcriptase", *Chemical Abstracts,* vol. 120, No. 17, p. 1160 (Apr. 25, 1994).

Tantillo, C. et al., 1994, *J Mol Biol, 243,* 369–387 Locations of Anti–AIDS Drug Binding Sites and Resistance Mutations in the Three–dimensional Structure of HIV–1 Reverse Transcriptase.

Tronchet, JMJ et al., "A QSAR Study Confirming the Heterogeneity of the HEPT Derivative Series Regarding Their Interaction with HIV Reverse Transcriptase", *Eur. J. Med. Chem.,* vol. 32, pp. 279–299 (1977).

Uckun, F. et al., "N–[2–(1–Cyclohexenyl)Ethyl]–N'–[2–(5–Bromopyridyl)]–Thiourea and N'–[2–(1–Cyclohexenyl)Ethyl]–N'–[2–(5–Chloropyridyl)]–Thiourea As Potent Inhibitors of Multidrug–Resistant Human Immunodeficiency Virus–1", *Bioorganic & Medicinal Chemistry Letters,* vol. 9 pp. 2721–2726, (1999).

Vig, R. et al., "5–Alkyl–2–[(Methylthiomethyl)Thio]–6–(Benzyl)–Pyrimidin–4–(1H)–Ones as Potent Non–Nucleoside Reverse Transcriptast Inhibitors of S–DABO Series", *Bioorganic & Medicinal Chemistry Letters 8,* pp. 1461–1466 (1998).

* cited by examiner

R-ISOMERS OF NONNUCLEOSIDE INHIBITORS

FIELD OF THE INVENTION

This invention relates to chiral derivatives of thiourea compounds, particularly of halopyridyl and thiazolyl thiourea compounds useful as potent non-nucleoside inhibitors of viral reverse transcriptase.

BACKGROUND OF THE INVENTION

Design of potent inhibitors of human immunodeficiency virus (HIV-1) reverse transcriptase (RT) activity, an enzyme responsible for the reverse transcription of the retroviral RNA to proviral DNA, has been a focal point in translational AIDS research efforts. Promising inhibitors include non-nucleoside inhibitors (NNI), which bind to a specific allosteric site of HIV-1 RT near the polymerase site and interfere with reverse transcription by altering either the conformation or mobility of RT, thereby leading to noncompetitive inhibition of the enzyme (Kohlstaedt, L. A. et al., *Science*, 1992, 256, 1783–1790). The inclusion of structural information in the drug design process should lead to more efficient identification of promising RT inhibitors.

A composite binding pocket constructed with the NNI binding site coordinates of multiple, varied RT-NNI structures was generated to facilitate the rational design of RT inhibitors (WO99/47501 published Sep. 23, 1999). This novel composite binding pocket, together with a computer docking procedure and a structure-based semi-empirical score function, provides a guide to predict the energetically favorable position of novel compounds in the NNI binding site of RT. Using this model, we have attempted to design a variety of novel, potent inhibitors of RT for therapeutic use.

The invention described herein recognizes a previously unknown preference for stereospecific isomers of certain NNI, and provides compounds, compositions, and methods comprising such stereospecific NNI.

SUMMARY OF THE INVENTION

The invention provides specific, potent stereospecific compounds as inhibitors of reverse transcriptase (RT) activity. The stereoisomers of the invention inhibit replication of retrovirus, such as human immunodeficiency virus (HIV). In one embodiment, the compounds and compositions of the invention are stereospecific, chiral derivatives of non-nucleoside inhibitors (NNI), specifically R-isomers. Preferred compounds are the R-isomers of carbocyclic or heterocyclic thiourea compounds. More preferred compounds include an electron withdrawing group, for example at $R_1$ of the compound shown as Formula I. Exemplary compounds of the invention are shown in the Examples below, and include R-isomers of halopyridyl and thiazolyl thiourea compounds.

The invention additionally provides compositions and methods for inhibiting reverse transcriptase (RT) activity of a retrovirus, such as HIV-I, by contacting the RT binding site of the retrovirus with a compound of the invention. The methods of the invention are useful for inhibiting replication of a retrovirus, such as HIV-1 and include treating a retroviral infection in a subject, such as an HIV-1 infection, by administering a stereospecific chiral compound or composition of the invention, for example, in a pharmaceutical composition.

The compounds of the invention may be combined with carriers and/or agents to enhance delivery to sites of viral infection, such as targeting antibodies, cytokines, or ligands. The compounds may include chemical modifications to enhance entry into cells, or may be encapsulated in various known delivery systems.

DETAILED DESCRIPTION OF THE INVENTION

Definitions

Figure 1A:
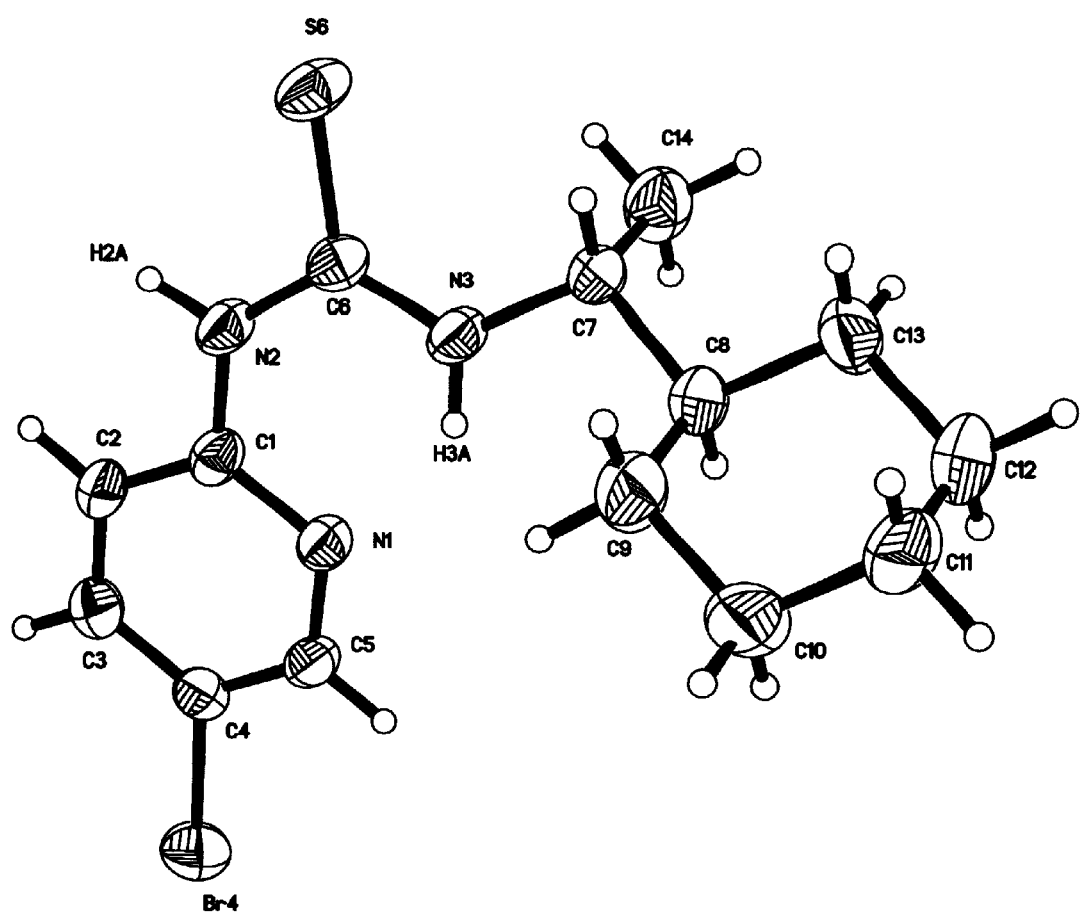
FIGS. 1A and 1B are schematic diagrams of X-ray crystal structures of compounds PHI-509R (FIG. 1A) and PHI-509S (FIG. 1B).

All scientific and technical terms used in this application have meanings commonly used in the art unless otherwise specified. As used in this application, the following words or phrases have the meanings specified.

As used herein, a "retrovirus" includes any virus that expresses reverse transcriptase. Examples of a retrovirus include, but are not limited to, HIV-1, HIV-2, HTLV-I, HTLV-II, FeLV, FIV, SIV, AMV, MMTV, and MoMuLV.

As used herein, "reverse transcriptase (RT)" refers to an enzyme having reverse transcriptase activity and an NNI binding site similar to that of HIV-1 RT and to which ligands that bind the composite binding pocket of the invention bind.

As used herein, "reverse transcriptase (RT) activity" means the ability to effect reverse transcription of retroviral RNA to proviral DNA. One means by which RT activity can be determined is by measuring viral replication. One measure of HIV-1 viral replication is the p24 core antigen enzyme immunoassay, for example, using the assay commercially available from Coulter Corporation/Immunotech, Inc. (Westbrooke, Mich.). Another means by which RT activity is analyzed is by assay of recombinant HIV-1 reverse transcriptase (rRT) activity, for example, using the Quan-T-RT assay system commercially available from Amersham (Arlington Heights, Ill.) and described in Bosworth, et al., *Nature* 1989, 341:167–168.

As used herein, a compound that "inhibits replication of human immunodeficiency virus (HIV)" means a compound that, when contacted with HIV-1, for example, via HIV-infected cells, effects a reduction in the amount of HIV-1 as compared with untreated control. Inhibition of replication of HIV-1 can be measured by various means known in the art, for example, the p24 assay disclosed herein.

As used herein, a "nonnucleoside inhibitor (NNI)" of HIV reverse-transcriptase (HIV-RT) means a compound that binds to an allosteric site of HIV-RT, leading to noncompetitive inhibition of HIV-RT activity.

As used herein, a "composite HIV reverse-transcriptase (RT) nonnucleoside inhibitor (NNI) binding pocket" or "composite binding pocket" means a model of the three-dimensional structure of a ligand binding site, such as the nonnucleoside inhibitor binding site of HIV-RT constructed from a composite of multiple ligand-binding site complexes. The composite binding pocket represents a composite molecular surface which reveals regions of flexibility within the binding site. Flexible residues within the NNI binding site include Tyr180, Tyr181, Tyr318, Tyr319, Phe227, Leu234, Trp229, Pro95, and Glu138 (the latter from the p51 subunit of RT). Examples of such a model include, but are not limited to, a composite molecular surface developed with the aid of computer software and based on a composite of coordinates of multiple RT-NNI complexes, as disclosed in published PCT Application No. WO99/47501.

As used herein, a "compound that fits the nonnucleoside inhibitor (NNI) pocket of reverse transcriptase (RT)" means a compound that substantially enters and binds the NNI binding site on RT. In one embodiment, a compound that fits the NNI pocket of RT inhibits RT activity. Generally, compounds that better fit the NNI pocket of RT contact a greater portion of the available molecular surface of the pocket and are more potent inhibitors of RT activity.

As used herein, "docking" a compound in a binding pocket means positioning a model of a compound in a model of the binding pocket. In one embodiment, the docking is performed with the use of computer software, such as the Affinity program within InsightII (Molecular Simulations Inc., 1996, San Diego, Calif.). Docking permits the identification of positions of the compound within the binding pocket that are favored, for example, due to minimization of energy.

As used herein, "minimization of energy" means achieving an atomic geometry of a molecule or molecular complex via systematic alteration such that any further minor perturbation of the atomic geometry would cause the total energy of the system as measured by a molecular mechanics force-field to increase. Minimization and molecular mechanics force-fields are well understood in computational chemistry (Burkert, U. and Allinger, N. L., Molecular Mechanics, *ACS Monograph*, 1982, 177, 59–78, American Chemical Society, Washington, D.C.).

As used herein, "gap space" means unoccupied space between the van der Waals surface of a compound positioned within the binding pocket and the surface of the binding pocket defined by residues in the binding site. This gap space between atoms represents volume that could be occupied by new functional groups on a modified version of the compound positioned within the binding pocket.

In the present invention, the terms "analog" or "derivative" are used interchangeably to mean a chemical substance that is related structurally and functionally to another substance. An analog or derivative contains a modified structure from the other substance, and maintains the function of the other substance, in this instance, maintaining the ability to interact with an NNI-RT binding site. The analog or derivative need not, but can be synthesized from the other substance.

As used herein, "halogen or halo" means fluoro, chloro, bromo, and iodo.

As used herein, "pharmaceutically acceptable salt" refers to a salt that retains the desired biological activity of the parent compound and does not impart any undesired toxicological effects. Examples of such salts include, but are not limited to, (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, flirmaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or (c) salts formed with an organic cation formed from N,N'-dibenzylethylenediamine or ethylenediamine; or (d) combinations of (a) and (b) or (c), e.g., a zinc tannate salt; and the like. The preferred acid addition salts are the trifluoroacetate salt and the acetate salt.

As used herein, "pharmaceutically acceptable carrier" includes any material which, when combined with a compound of the invention, allows the compound to retain biological activity, such as the ability to inhibit RT activity, and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well-known conventional methods (see, for example, Remington's Pharmaceutical Sciences, Chapter 43, 14th Ed., Mack Publishing Col, Easton Pa. 18042, USA).

Screening of Candidate Compounds

Candidate chiral inhibitors of the invention can be evaluated for their anti-viral activity using conventional techniques. Evaluation of inhibitor binding to the binding pocket model typically involves determining the location and binding proximity of a given moiety, the occupied space of a bound inhibitor, the deformation energy of binding of a given compound, and electrostatic interaction energies. Examples of conventional techniques useful in the above evaluations include, but are not limited to, quantum mechanics, molecular dynamics, Monte Carlo sampling, systematic searches, and distance geometry methods (Marshall, G. R., *Ann. Rev. Pharmacol. Toxicol.*, 1987, 27, 193). Examples of computer programs for such uses include, but are not limited to, Gaussian 92, revision E2 (Gaussian, Inc. Pittsburgh, Pa.), AMBER version 4.0 (University of California, San Francisco), QUANTA/CHARMM (Molecular Simulations, Inc., Burlington, Mass.), and Insight II/Discover (Biosym Technologies Inc., San Diego, Calif.). These programs may be implemented, for example, using a Silicon Graphics Indigo2 workstation or IBM RISC/6000 workstation model 550. Other hardware systems and software packages will be known and of evident applicability to those skilled in the art.

Chiral inhibitors that are identified or designed by the methods of the invention can be tested for their anti-HIV or anti-RT activity using one of the standard in vitro assays known in the art, such as the p24 enzyme immunoassay disclosed herein.

The invention provides compounds useful as inhibitors of RT, particularly viral RT, more particularly retroviral RT, and specifically HIV-RT, such as HIV-1 RT. The inhibitory compounds of the invention are chiral derivatives of NNI, more particularly R-isomers of carbocyclic and heterocyclic thiourea compounds, for example R-isomers of halopyridyl and thiazolyl thiourea compounds that provide a good fit into the NNI-RT composite binding pocket.

COMPOUNDS OF THE INVENTION

Compounds of the invention are those having the general formula I shown below, and providing a good fit into the NNI-RT binding pocket, as described above.

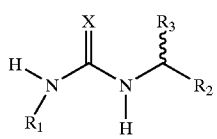

(I)

X is S or O. $R_1$ is a carbocyclic or heterocyclic ring, the ring preferably containing 5 or 6 members, that may be saturated or unsaturated with one to three double bonds; the ring may be substituted, preferably with a halogen, and most preferably with bromo or chloro, or unsubstituted; and may contain one or more S or N atom in the ring. The substituent on ring $R_1$ preferably increases an electron withdrawing effect at this portion of the molecule. $R_1$ can be, for example, phenyl, pyridyl, pyrimidinyl, pyridazinyl, thiazolyl, isothiazolyl, tetrazolyl, naphthyl, imidazolyl, pyrrole, cyclohexenyl, naphthyl indolyl, thienyl, piperazinyl, morpholyl, furyl, adamantyl, piperonyl, and the like compounds, with the proviso that these compounds have a structure permitting fit into the geometry of the NNI-RT binding pocket and provide anti-viral activity.

In a preferred embodiment, $R_1$ is halopyridyl or thiazoyl. Lead compounds of the invention include those where $R_1$ is

or

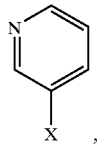

where X is preferably halo, most preferably bromo or chloro.

$R_2$ is a carbocyclic ring able to adopt a planar configuration, preferably containing 5 or 6 members. The ring may be saturated or unsaturated, and may be substituted. $R_2$ can be, for example, phenyl, cyclohexyl, cyclohexenyl, cyclopentyl, and the like planar rings.

$R_3$ is an aryl, heteroaryl, alkyl, or halo (F, Br, Cl, I), and is preferably a $C_1$–$C_3$ alkyl, more preferably $CH_3$, $CH_3 CH_2$, CH $(CH_3)_2$, or a phenyl, naphthyl, or a carbocyclic or heterocyclic ring, which is saturated or unsaturated, preferably unsaturated, and may be substituted, for example with electron withdrawing groups such as halo, or electron donating groups, such as OH, OMe, $NH_2$, $CH_3$, $Ch_3CH_2$, $CH(CH_3)_2$, and the like. The heterocyclic ring may be, for example, one of the following:

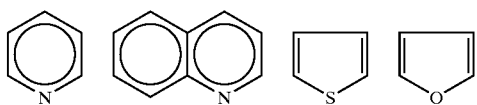

-continued

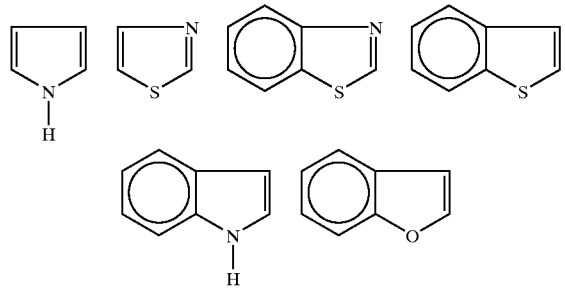

In the lead compounds of the invention, $R_3$ is $CH_3$.

The chiral R-isomer compounds of the invention are fit in the NNI-RT binding pocket, and do so with a better fit than their counterpart S-isomers. Most preferably, a compound of the invention complexed with an NNI-RT binding pocket has a predicted $K_i$ of less than about 1 $\mu$M, for example, calculated as described in the in the docking assays of the Examples herein.

Specific compounds of the invention include:

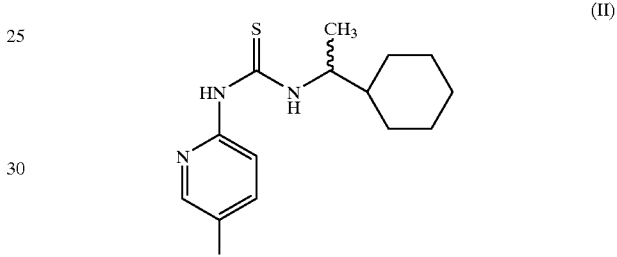

(II)

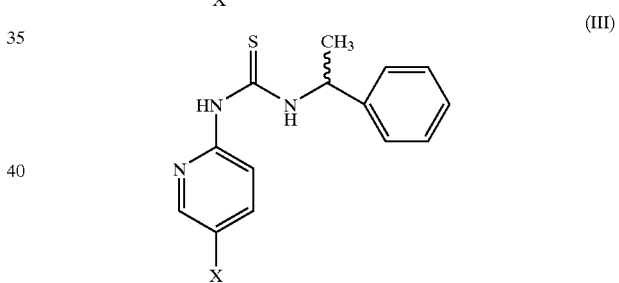

(III)

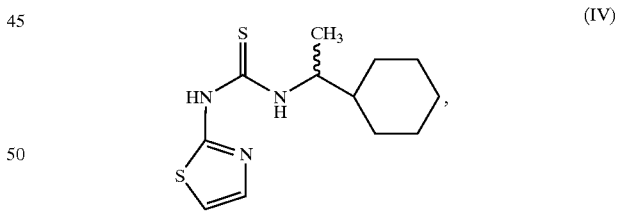

(IV)

where X is halo, preferably bromo or chloro. Compounds of the invention are further described in the Examples below.

SYNTHESIS OF COMPOUNDS

The stereospecific chiral compounds of the invention can be synthesized by known methods, for example, following the Synthetic Scheme shown in the Examples below. The stereoisomers can be isolated by a variety of known methods, for example, by chiral chromatography such as GC, HPLC, and SFC; crystallizaton with an enantiomerically pure acid or base; preferential crystallization via seeding with a purified enantiomer; enantio-selective enzymatic separation, and the like methods to separate R and S-isomers.

ANTIVIRAL COMPOSITIONS

The stereospecific chiral compounds of the invention have the ability to inhibit replication of a retrovirus, such as human immunodeficiency virus (HIV), preferably with an $IC_{50}$ of less than 50 µM, for example, as determined by p24 enzyme immunoassay described in the Examples below. More preferably, the stereospecific compounds of the invention inhibit replication of HIV in the p24 assay with an $IC_{50}$ of 1 to 5 µM, or less. Most preferably, the stereospecific compounds inhibit replication of HIV in the p24 assay with an $IC_{50}$ of less than 5 nM. In some embodiments, the stereospecific compounds inhibit replication of HIV in the p24 assay with an $IC_{50}$ of less than 1 nM.

The invention provides a composition enriched with a stereospecific chiral compound of the invention, or a pharmaceutically acceptable salt or ester thereof, and optionally, pharmaceutically acceptable carrier. Preferably, the composition of the invention contains little or no S-isomer, but is enriched to provide a greater amount of the active antiviral R-isomer of the invention, preferably at least 70%, and preferably at least 90% of the R-isomer to S-isomer. Compositions of the invention are useful for prevention and treatment of retroviral infection, such as HIV infection and/or for inhibiting replication of retrovirus.

METHODS OF USING COMPOUNDS OF THE INVENTION

The compounds of the invention are useful in methods for inhibiting reverse transcriptase activity of a retrovirus. Retroviral reverse transcriptase is inhibited by contacting RT in vitro or in vivo, with an effective inhibitory amount of a compound of the invention. The compounds of the invention also inhibit replication of retrovirus, particularly of HIV, such as HIV-1. Viral replication is inhibited, for example, by contacting the virus with an effective inhibitory amount of a compound of the invention.

Because the compounds of the invention inhibit retroviral replication and inhibit retroviral RT activity, the invention provides a method for treating or preventing retroviral infection, such as HIV infection, and a method for treating AIDS or AIDS-related complex (ARC). The method comprises administering to a subject an effective inhibitory amount of a compound of the invention or a pharmaceutically acceptable salt or ester of the compound. The compound or inhibitor of the invention is preferably administered in combination with a pharmaceutically acceptable carrier, and may be combined with specific delivery agents, including targeting antibodies and/or cytokines. The compound or inhibitor of the invention may be administered in combination with other antiviral agents, immunomodulators, antibiotics or vaccines.

The stereospecific chiral compounds of the invention can be administered orally, parentally (including subcutaneous injection, intravenous, intramuscular, intrasternal or infusion techniques), by inhalation spray, topically, by absorption through a mucous membrane, or rectally, in dosage unit formulations containing conventional non-toxic pharmaceutically acceptable carriers, adjuvants or vehicles. Pharmaceutical compositions of the invention can be in the form of suspensions or tablets suitable for oral administration, nasal sprays, creams, sterile injectable preparations, such as sterile injectable aqueous or oleagenous suspensions or suppositories.

For oral administration as a suspension, the compositions can be prepared according to techniques well-known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents and lubricants known in the art.

For administration by inhalation or aerosol, the compositions can be prepared according to techniques well-known in the art of pharmaceutical formulation. The compositions can be prepared as solutions in saline, using benzyl alcohol or other suitable preservatives, absorption promoters to enhance bioavailability, fluorocarbons or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquify or dissolve in the rectal cavity to release the drug.

Dosage levels of approximately 0.02 to approximately 10.0 grams of a compound of the invention per day are useful in the treatment or prevention of retroviral infection, such as HIV infection, AIDS or ARC, with oral doses 2 to 5 times higher. For example, HIV infection can be treated by administration of from about 0.1 to about 100 milligrams of compound per kilogram of body weight from one to four times per day. In one embodiment, dosages of about 100 to about 400 milligrams of compound are administered orally every six hours to a subject. The specific dosage level and frequency for any particular subject will be varied and will depend upon a variety of factors, including the activity of the specific compound the metabolic stability and length of action of that compound, the age, body weight, general health, sex, and diet of the subject, mode of administration, rate of excretion, drug combination, and severity of the particular condition.

The compounds of the invention can be administered in combination with other agents useful in the treatment of HIV infection, AIDS or ARC. For example, the compounds of the invention can be administered in combination with effective amounts of an antiviral, immunomodulator, anti-infective, or vaccine. The compounds of the invention can be administered prior to, during, or after a period of actual or potential exposure to retrovirus, such as HIV.

ADVANTAGES OF THE INVENTION

The chiral compounds of the invention are useful for inhibition of RT activity and for inhibition of retroviral replication. The R-isomeric compounds disclosed herein provide more potent NNI of RT than their S-isomeric counterparts.

In addition, the compounds of the invention provide a higher selectivity index (S.I.>$10^5$) than currently available anti-HIV compounds. This high S.I. permits more effective antiviral activity with a minimum of adverse cytotoxic effects.

EXAMPLES

The following examples are presented to illustrate the present invention and to assist one of ordinary skill in making and using the same. The examples are not intended in any way to otherwise limit the scope of the invention.

Example 1

Modeling Procedure
Construction of the Composite NNI binding pocket

A novel model of the NNI binding pocket of RT was constructed by superimposing nine individual RT-NNI crystal structures and generating a van der Waals surface that encompassed all the overlaid ligands. This "composite binding pocket" surprisingly revealed a different and unexpectedly larger NNI binding site than shown in or predictable from any of the individual structures and serves as a probe to more accurately define the potentially usable space in the binding site (WO99/47501).

Predictable Activities

The trend of the calculated $K_i$ values based on the modeling and on the use of the composite binding pocket, with surprising accuracy, predicted the trend of the experimentally determined $IC_{50}$ values from HIV replication assays. Compounds were tested for RT inhibitory activity in cell-free assays using purified recombinant HIV RT (listed as $IC_{50}[rRT]$), as well as by in vitro assays of anti-HIV activity in HTLV$_{IIIB}$-infected peripheral blood mononuclear cells ($IC_{50}[p24]$) (Zarling, J. M. et al., Nature, 1990, 347, 92–95; Erice, A. et al., Antimicrob. Ag. Chemother., 1993, 37, 835; Uckun, F. M. et al., Antimicrobial Agents and Chemotherapy, 1998, 42, 383).

Compounds which better fit the composite binding pocket as composed to known NNI, and have lower calculated $K_i$ values show better $IC_{50}[rRT]$ values. The same trend is also observed for $IC_{50}[p24]$ values.

Example 2

Synthesis of Test Compounds
Materials and Methods

We previously reported the construction of a novel computer model of the non-nucleoside inhibitor (NNI) binding pocket of the HIV reverse transcriptase (RT).[1-11]. See also WO99/47501. We used this model together with a computer docking procedure and a structure-based semi-empirical score function as a guide to predict energetically favorable positions of new NNIs, as described.[1-11]

All chemicals were used as received from Aldrich Chemical Company (Milwaukee, Wis.). All reactions were carried out under nitrogen. Column chromatography was performed using EM Science silica gel 60 and one of the following solvents: ethyl acetate, methanol, chloroform, hexane, or methylene chloride. Nuclear magnetic resonance (NMR) spectra were recorded on a Varian (Palo Alto, Calif.) 300 MHz instrument (Mercury 2000 model) and chemical shifts are reported in parts per million (ppm) relative to tetramethylsilane as an internal standard at 0 ppm. $^{13}$C NMR spectra were recorded at 75 MHz in CDCl$_3$ on the same instrument using a proton decoupling technique. The chemical shifts reported for $^{13}$C NMR are referenced to the chloroform triplet at 77 ppm. Melting points were measured using a Mel-Temp 3.0 (Laboratory Devices Inc., Holliston, Mass.) melting apparatus and are uncorrected. UV spectra were recorded from a Beckmann (Fullerton, Calif.) model DU 7400 UV/Vis spectrometer using a cell path length of 1 cm and methanol solvent. Fourier Transform Infrared spectra were recorded using an FT-Nicolet (Madison, Wis.) model Protege 460 instrument. Mass spectrum analysis was performed using a Hewlett-Packard (Palo Alto, Calif.) Matrix Assisted Laser Desorption time-of-flight (MALDI-TOF) spectrometer (model G2025A) in the molecular ion detection mode (matrix used was cyanohydroxycinnamic acid). Some samples were analyzed using a Finnigan (Madison, Wis.) MAT 95 instrument. Elemental analysis was performed by Atlantic Microlabs (Norcross, Ga.).

Chemical Synthesis

For the synthesis of the thiourea compounds, the general procedure shown in Scheme 1 and as previously reported[2] was followed.

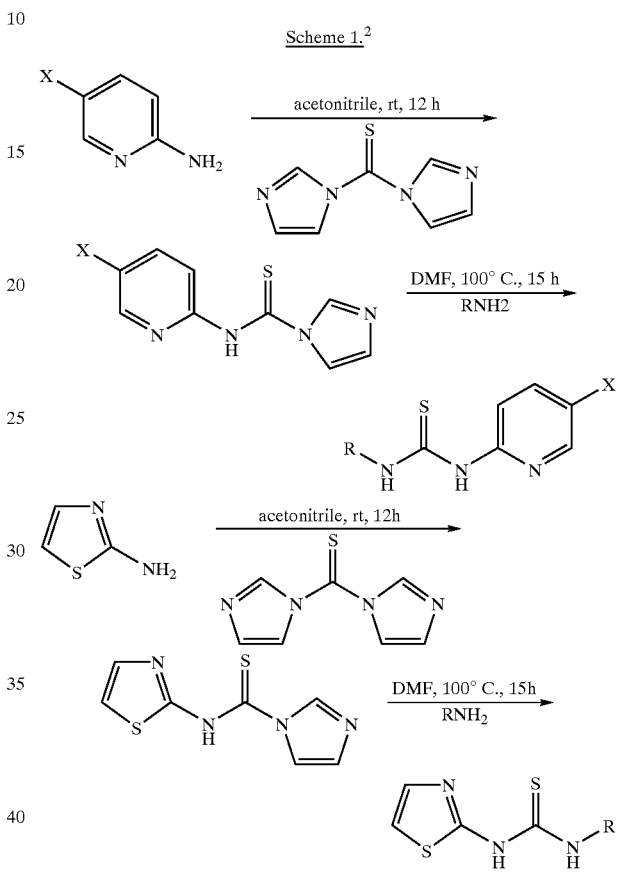

Scheme 1.[2]

Physicochemical Properties:

N-[1-(1-(1R)-Cyclohexylethyl)]-N-[2-(5-bromopyridyl)]thiourea (PHI-509$^R$).

Yield 32%, mp: 176–177° C.; UV (MeOH) $\lambda_{max}$ 206,210, 275 nm; IR: 3207, 3151, 3078, 3026, 2979, 2925, 2850, 1593, 1556, 1467, 1353, 1305, 1270, 1226, 1176, 1134, 1095, 1006, 960, 925, 862, 827, 731 cm$^{-1}$; $^1$H NMR (CDCl$_3$) δ 11.32 (d, 1H, J=8.7), 9.70 (s, 1H), 8.16 (d, 1H, J=9), 4.40–4.33 (m, 1H), 1.85–1.48 (m, 7H), 1.18–1.16 (d, 3H, J=6.6), 1.21–0.98 (m, 4H); $^{13}$C NMR (CDCl$_3$) δ 177.6, 152.0, 146.1, 140.9, 113.8, 112.4, 56.1, 42.7, 29.1, 29.0, 26.5, 26.3, 26.2, 17.1; MS (MALDI-TOF) 344.4 (C$_{14}$H$_{20}$BrN$_3$S+2).

N-[1-(1-(1S)-N-[1-(1(1R)-Cyclohexylethyl)]-N-[2-(5-chloropyridyl)]thiourea (PHI-510$^R$).

Yield 29%, mp: 144–145° C.; UV (MeOH) $\lambda_{max}$ 202, 207, 211, 256, 273, 304 nm; IR::3210, 3024, 2931, 2850, 1601, 1549, 1474, 1230, 1108, 823 cm$^{-1}$; $^1$H NMR (DMSO-d$_6$) δ 11.2 8(d, 1H, J=8.4), 10.62 (s, 1H), 8.25 (d, 1H, J=2.7), 7.86–7.82 (dd, 1H, J=8.7), 7.18 (t, 1H), 4.32–4.24 (m, 1H), 1.70–1.56 (m, 7H), 1.21–1.10 (d, 3H, J=6.6), 1.18–0.99 (m, 4H); $^{13}$C NMR (DMSO-d$_6$) δ 178.8, 152.9, 144.4, 139.4, 124.2, 114.7, 55.5, 42.8, 29.5, 29.4, 26.8, 26.6, 26.5, 17.7; MS (MALDI-TOF) 298.6 (C$_{14}$H$_{20}$ClN$_3$S+1).

N-[1-(1R)-(1-α-methylbenzyl]-N'-[2-(5-bromopyridyl)] thiourea (PHI-511$^R$).

Yield 43%, mp: 170–172° C.; UV $\lambda_{max}$ 211, 257, 275, 278 nm; IR:3245, 3027, 2979, 2925, 1594, 1525, 1475, 1188, 704 cm$^{-1}$; $^1$H NMR (DMSO-d$_6$) δ 11.79 (d, 1H), 10.76 (s, 1H), 8.39 (d, 1H, J=2.1), 7.98 (dd, 1H, J=9), 7.35 (d, 4H, J=3.9), 7.28–7.23 (m, 1H), 7.15 (d, 1H, J=9), 5.55 (q, 1H), 1.51 (d, 3H); $^{13}$C NMR(DMSO-d$_6$) δ 178.4, 152.5, 146.2, 143.2, 141.5, 128.6, 127.0, 126.1, 114.7, 112.0, 54.0, 22.7; MALDI-TOF: 337.7.

N-[1-(1-(1R)-α-methylbenzyl]-N'-[2-(5-chloropyridiyl)] thiourea (PHI-512$^R$).

Yield 44%, mp: 185–187.5° C.; UV $\lambda_{max}$ 204, 255, 275,305 nm; IR; 3247. 3169, 3087, 2978, 1600, 1529, 1483, 1189, 1034, 822, 761, 694 cm$^{-1}$; $^1$H NMR (CDCl$_3$) δ 11.77 (d, 1H), 9.47 (s, 1H), 8.12 (d, 1H, J=2.1), 7.53 (dt, 1H, J=8.7), 7.40–7.26 (m, H), 6.85 (d, 1H, J=8.7), 5.73–5.64(m, 1H), 1.65 (d, 3H, J=6.9); $^{13}$C NMR (CDCl$_3$) δ 178.4. 151.8, 142.8, 144.4, 138.8, 128.9, 127.5, 126.4, 125.4, 113.6, 55.3, 22.7; MALDI-TOF: 293.7.

N-[1-(1-(1R)-Cyclobexyl)ethyl]-N'-[2-(thiazolyl)] thiourea (PHI-513$^R$)

Yield 45%; mp: 118–119° C.; V (MeOH) $\lambda_{max}$: 204, 259, 288 nm; IR: 3170, 3040, 2968, 2927, 2849, 1656, 1514 cm$^{-1}$; $^1$H NMR (CDCl$_3$) δ 10.87, (s, 2H), 7.31 (d, 1H, J=3.6), 6.81 (d, 1H, J=3.6), 4.47–4.36 (m, 1H), 1.87–1.53 (m, 4H), 1.24 (d, 3H, J=6.6), 1.40–1.32 (m, 5H); $^{13}$C NMR (CDCl$_3$) δ 176.3, 162.2, 137.9, 111.2, 56.4, 43.1, 29.5, 29.3, 26.8, 26.6, 26.5, 17.5; MALDI-TOF 271.2.

N-[1-(1-(1R)-Cyclohexylethyl]-N'-[2-(pyridyl)]thiourea PHI-543).

Yield 28%, mp: 125–127° C.; UV (MeOH) $\lambda_{max}$: 206, 211, 249, 266, 294 nm; IR: 3212, 3169, 3031, 2925, 2850, 1600, 1556, 1531, 1493, 775 cm$^{-1}$; $^1$H NMR (DMSO-d$_6$) δ 11.98 (d, 1H), 9.12 (s, 1H), 8.14 (dd, 1H, J=4.8), 7.64–7.58 (m, 1H), 6.96–6.86 (m, 2H), 4.49–4.37 (m, 1H), 1.86–1.54 (m, 5H), 1.24 (d, 3H), 1.30–1.06 (m, 6H); $^{13}$C NMR (DMSO-d$_6$) δ 178.4, 153.8, 145.8 138.7, 117.9, 112.4, 56.4, 43.2, 29.5, 29.4, 26.9, 26.7, 26.6, 17.5; MALDI-TOF 264.8.

X-Ray Crystallography

Figure 1B:
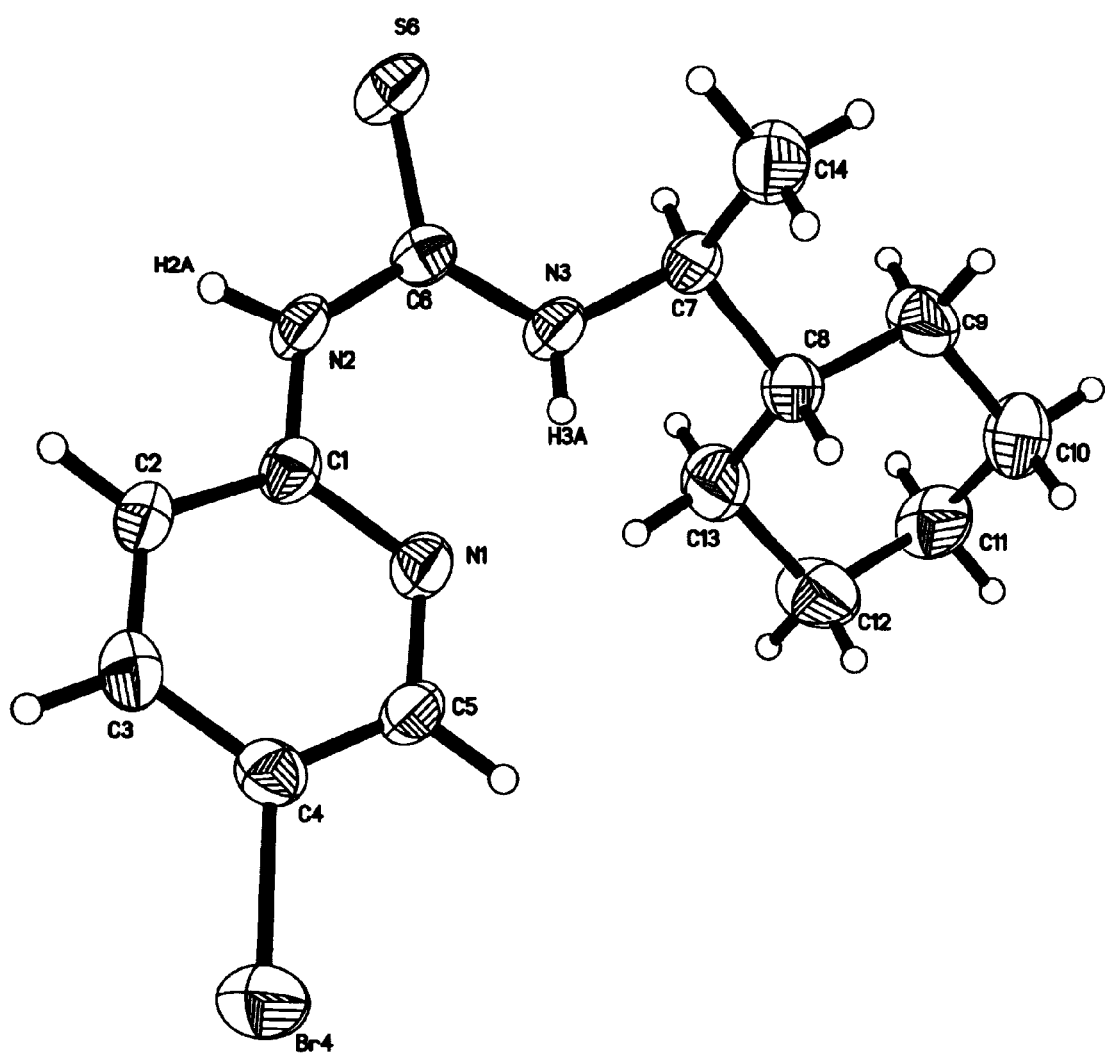

The structures of the chiral bromopyridyl thiourea compounds PHI-509$^R$ and PHI-509$^S$ were resolved by X-ray crystallography[11], and are diagrammatically shown in FIGS. 1A and 1B. Both compounds adopt lower energy conformations in the crystalline state relative to the C14-C7-C8-C13 torsion angle [62.0(5)°] in PHI-509$^R$ and the C14-C7-C8-C9 torsion angle [−62.4(5)°] in PHI-509$^S$, with staggering of the cyclohexyl and methyl groups on the chiral carbon.

Molecular Modeling

Molecular modeling studies were performed and test compounds were positioned into the RT active site by a docking procedure as described previously (WO99/47501). Once the final, energetically favored docked position of the molecule in the NNI site was determined, a LUDI score was assigned, from which an estimation of the inhibition constant (K$_i$ value) was determined. The calculated K$_i$ values shown in Table 1, below, suggested that the R-isomers of the test compounds would be active inhibitors of RT, while the S-isomers would not.

Figure 2A:
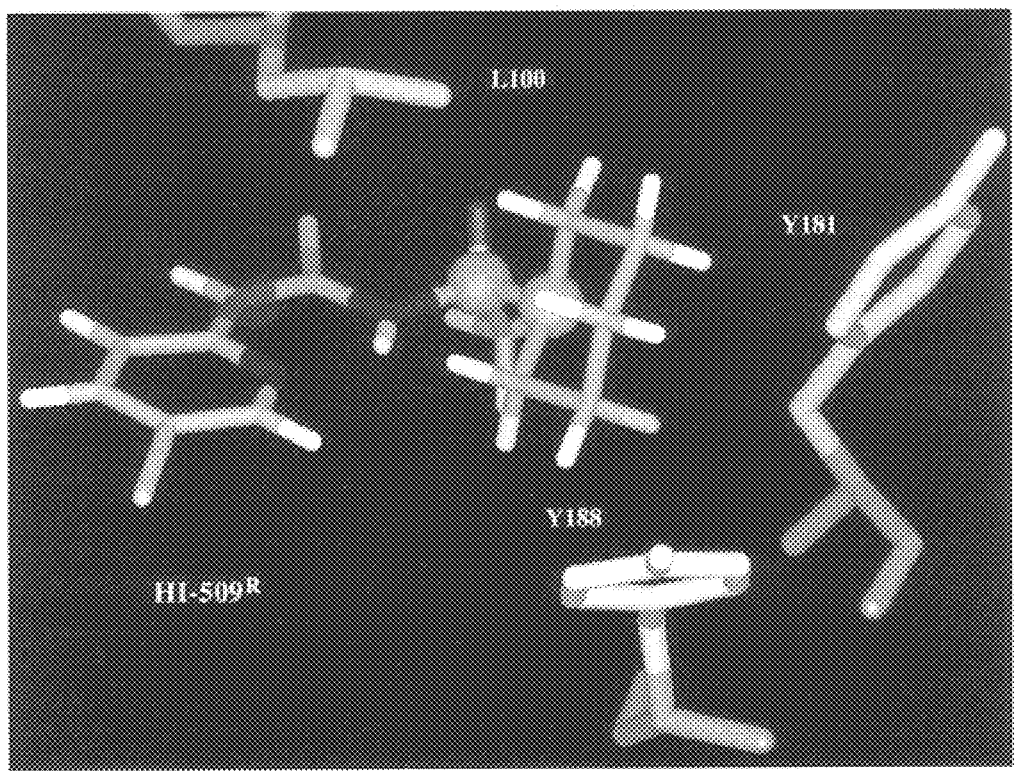
FIGS. 2A and 2B are computer generated images showing the docking of PHI-509R (FIG. 2A) and PHI-509S (FIG. 2B) to the NNI binding pocket of HIV-RT. The relative proximity of the stereospecific compounds to selected residues of the RT pocket (L100, Y181, and Y188) is shown.
Figure 2B:
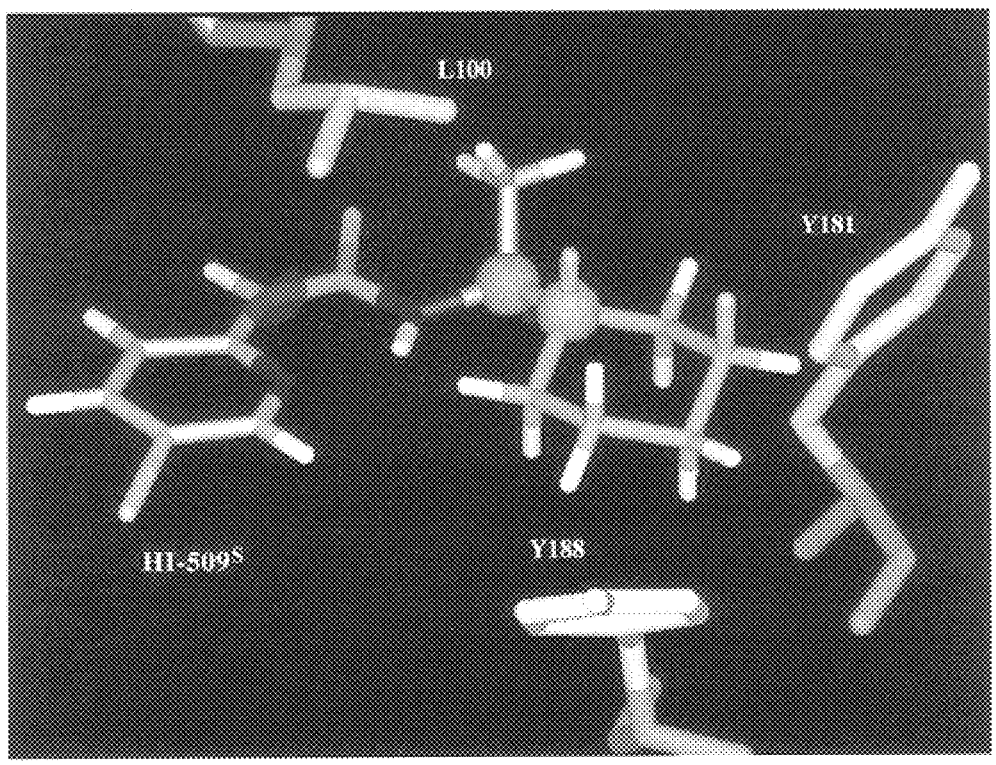

Computer generated stick models of the test compounds docked in the NNI binding pocket are shown in FIGS. 2A and 2B. The data indicated that the R-isomer (PHI-509$^R$) would fit the target NNI binding pocket on HIV-RT much better than its enantiomer (PHI-509$^S$). Unfavorable steric interactions with the NNI binding pocket residues near the Y181 side chain would impair the binding of PHI-509$^S$ in a lower energy "staggered" conformation. This steric hindrance would be relieved if PHI-509$^S$ adopts an energetically unfavorable "eclipsed" conformation. In either case, the estimated binding energy would be significantly higher for PHI-509$^S$, as reflected by the higher estimated K$_i$ value, as shown in Table 1. Similar assumptions could be made in favor of the R-isomer in modeling studies of the chiral chloropyridyl thiourea compounds:

N-[1-(1-(1R)-cyclohexylethyl)]-N-[2-(5-chloropyridyl)] thiourea (PHI-510$^R$) and N-[1-(1-(1S)-cyclohexylethyl)]-N-[2-(5-chloropyridyl)] thiourea (PHI-510$^S$).

Modeling studies indicated that the methyl group on the chiral carbon of PHI-509$^R$/PHI-510$^R$ likely promotes its strong binding to the NNI binding pocket via van der Waals contacts with residue V179. Since this methyl group is 7 Å away from Y181, 9 Å from Y188, 8.5 Å from V106, and 6.5 Å from K103, as measured from the carbon atom of the methyl group to the C☐ position of the protein residue, its favorable impact on the binding of PHI-509$^R$/PHI-510$^R$ to RT should not be affected by frequently encountered mutations involving these residues.

As shown in Table 1, control compounds with unsubstituted pyridyl rings were predicted to fit poorly into the NNI binding pocket (Estimated K$_i$). Modeling studies indicated that the Wing 2 group influences the orientation of the Wing 1 group and a local change may be translated to overall positional rearrangement. It was found that the unsubstituted thiazole can be better accommodated the binding site than unsubstituted pyridine (in combination with the bulky cyclohexylethyl group) as a whole molecule. On the other hand, halogen substitution on pyridine adds a considerable number of favorable interactions at the Wing 1 region, which improved the final interaction score for the substituted pyridine thiourea compounds. Along these same lines, a proper substitution, for example with halogen on the thiazole group is expected to produce active compounds.

Antiviral Activity

The accuracy of the predictions of the modeling studies was evaluated in cell free RT inhibition assays. The HIV-1 strain HTLV$_{IIIB}$ (kindly provided by Dr. Neal T. Wetherall, VIROMED Laboratories, Inc.), was propagated in CCRF-CEM cells, and used in in vitro assays of the anti-HIV-1 activity of the synthesized compounds of the invention. Cell-free supernatants of HTLV$_{IIIB}$-infected CCRF-CEM cells were harvested, dispensed into 1 ml aliquots, and frozen at −70° C. Periodic titration of stock virus was performed by examining its cytopathic effects in MT-2 cells following the procedures described in (Erice, et al., *Antimicrob. Ag. Chemother.*, 1993, 37, 835).

Normal human peripheral blood mononuclear cells (PBMNC) from HIV-negative donors were cultured 72 hours in RPMI 1640 supplemented with 20%(v/v) heat-inactivated fetal bovine serum (FBS), 3% interleukin-2, 2 mM L-glutamine, 25 mM HEPES, 2 g/L NaHCO$_3$, 50 μg/ml gentamicin, and 4 μg/ml phytohemagglutinin prior to exposure to HIV-1. The incubated cells were then exposed to HIV-1 at a multiplicity of infection (MOI) of 0.1 during a one-hour adsorption period at 37° C. in a humidified 5% CO$_2$ atmosphere. Subsequently, infected cells were cultured in 96-well microtiter plates (100 μl/well; 2×10$^6$ cells/ml) in the presence of test compounds, including appropriate controls. Aliquots of culture supernatants were removed from the wells on the seventh day after infection for p24 antigen assays. The methods used in the P24 assay were as previously described in Uckun, et al., *Antimicrobial Agents and Chemotherapy*, 1998, 42, 383; Zarling, et al., *Nature*, 1990, 347, 92–95; Erice, et al., *Antimicrob. Ag. Chemother.*, 1993, 37, 835.

The applied p24 enzyme immunoassay (EIA) was the unmodified kinetic assay commercially available from Coulter Corporation/Immunotech, Inc. (Westbrooke, Me.). In the assay, a murine monoclonal antibody against HIV core protein is coated onto microwell strips. Antigen (HIV core protein) present in the test culture supernatant samples binds the antibody and the bound antibody-antigen complex is quantitated. Percent viral inhibition was calculated by comparing the p24 values from the test substance-treated infected cells with p24 values from untreated infected cells (i.e., virus controls).

In addition, the activity of the test compounds to inhibit recombinant HIV-1 reverse transcriptase (rRT) activity was determined using the Quan-T-RT assay system (Amersham, Arlington Heights, Ill.), which utilizes the scintillation proximity assay principle. The assay method is described in Bosworth, N., et al., *Nature*, 1989, 341, 167–168. Data for both bioassays is reported as $IC_{50}$ values.

In parallel with the bioactivity assays, the effects of the test compounds on cell viability was also examined, using the Microculture Tetrazolium Assay (MTA) described in Darling, et al., *Nature*, 1990, 347, 92–95; Erice, et al., *Antimicrob. Ag. Chemother.*, 1993, 37, 835. In brief, non-infected PBMNC were treated with test compounds or controls for 7 days under identical experimental conditions and 2,3-bis(2-methoxy-4-nitro-5-sulfophenyl)-5-[(phenylamino)-carbonyl]-2H-tetrazolium hydroxide (XTT), was added to quantitative cellular proliferation.

A computer simulation of the binding of the target compounds into the NNI binding site of RT was accomplished using a molecular docking procedure. Docking of the compounds into the NNI binding site utilized X-ray coordinates of the composite RT/NNI.

Antiviral Activity Data

As shown in Table 1, PHI-509$^R$ and PHI-510$^R$, with estimated $K_i$ values 100-fold lower than those of the S-isomers, inhibited recombinant RT in vitro with 100-fold lower $IC_{50}$ values. The control compounds with unsubstituted pyridyl rings did not exhibit detectable RT inhibitory activity (Table 1).

We next examined the ability of R-isomers PHI-509$^R$ and PHI-510$^R$ to inhibit the replication of the HIV-1 strain HTLV$_{IIIB}$ in human peripheral blood mononuclear cells (PBMC). Both PHI-509$^R$ and PHI-510$^R$ inhibited HIV-1 replication with $IC_{50}$ values of 0.001 μM and 0.025 μM, respectively. In contrast, the $IC_{50}$ values of the S-isomers (PHI-509$^S$ and PHI-510$^S$) and the control compounds with unsubstituted pyridyl rings (PHI-542 and PHI-543) were >1 μM (Table 1). Similarly the R-isomers (but not S-isomers) of the α-methyl benzyl halopyridyl compounds PHI-511 and PHI-512 exhibited potent activity both in cell-free RT inhibition assays and cellular HIV-1 replication assays (Table 1).

The substitution of the pyridyl ring of PHI-509$^R$ and PHI-510$^R$ with a thiazolyl ring (compound PHI-513$^R$) resulted in 10-fold higher $K_i$ values and 10-fold higher $IC_{50}$ values in cell free RT inhibition assays. The S-isomer, with an estimated $K_i$ value of >100 μM, did not exhibit any RT inhibitory activity, even at 100 μM. Taken together, these results provide unprecedented evidence that the stereochemistry of a thiourea compound can profoundly affect its ability to fit into the NNI binding pocket of RT, and therefore affect its anti-HIV activity.

TABLE 1

Effect of stereochemistry on anti-HIV activity of thiourea compounds.[a]

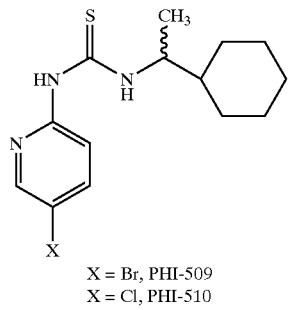

X = Br, PHI-509
X = Cl, PHI-510

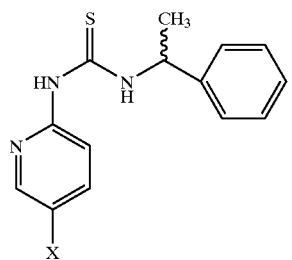

X = Br, PHI-511
X = Cl, PHI-512

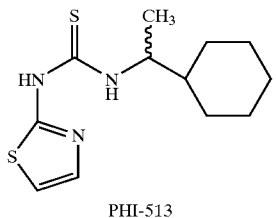

PHI-513

| Compound | Isomer | X | Estimated $K_i$ $(\mu M)^b$ | rRT | $HTLV_{IIIB}$ | RT-MDR | A17 | A17 |
|---|---|---|---|---|---|---|---|---|
| PHI-509$^R$ | R | Br | 1.1 | 1.2 | 0.001 | 0.2 | 0.4 | 10.0 |
| PHI-509$^S$ | S | Br | >100 | >100 | >1 | N.D. | N.D. | N.D. |
| PHI-510$^R$ | R | Cl | 1.2 | 1.4 | 0.025 | 0.06 | 0.07 | 8.2 |
| PHI-510$^S$ | S | Cl | >100 | >100 | >1 | N.D. | N.D. | N.D. |
| PHI-542 | S | H | >100 | >100 | >1 | N.D. | N.D. | N.D. |
| PHI-543 | R | H | >100 | >100 | >1 | N.D. | N.D. | N.D. |
| PHI-511$^R$ | R | Br | N.D. | 1.6 | 0.01 | 0.005 | 0.01 | 2.7 |
| PHI-511$^S$ | S | Br | N.D. | >100 | >1 | N.D. | N.D. | N.D. |
| PHI-512$^R$ | R | Cl | N.D. | 1.2 | 0.010 | 0.010 | 0.2 | 10.2 |
| PHI-512$^S$ | S | Cl | N.D. | >100 | N.D. | N.D. | N.D. | N.D. |
| PHI-513$^R$ | R | NA | 12.0 | 13.0 | 0.001 | 5.6 | 0.9 | 5.8 |
| PHI-513$^S$ | S | NA | >100 | >100 | >1 | N.D. | N.D. | N.D. |
| Nevirapine | NA | NA | N.D. | 23 | 0.034 | 5.0 | >100 | >100 |
| Trovirdine | NA | NA | 0.6 | 0.8 | 0.007 | 0.02 | 0.5 | >100 |
| Delavirdine | NA | NA | N.D. | 1.5 | 0.009 | 0.4 | 50.0 | >100 |
| HI-240 | NA | NA | 0.6 | 0.6 | <0.001 | 0.005 | 0.2 | 41.0 |

[a]The anti-HIV activity was measured by determining the inhibition of the HIV-1 strain $HTLV_{IIIB}$ in human PBMC as previously described in detail.[5] H9 cells instead of PBMC were used for the RT-MDR experiments. The cell-free RT inhibition assays using recombinant RT (rRT) and the Quan-RT assay kit (Amersham, Arlington Heights, IL) were performed as reported.[5]
[b]$K_i$ values were estimated based on our previously published procedures.[2–7]
N.D. not determined.
NA not applicable.

Activity Against NNI-Resistant Strains

We also examined the activity of the lead compounds PHI-509$^R$, PHI-510$^R$, PHI-511$^R$, PHI-512$^R$, and PHI-513$^R$ against three NNI-resistant HIV-1 strains. Each of the test R-isomers was more active than nevirapine or delavirdine against the drug resistant HIV-1 strains. The most active agent against drug-resistant HIV-1 strains was PHI-511$^R$. Test compound PHI-511$^R$ was as active against the NNI-resistant HIV-1 strain A17 (with a Y181C mutation) as it was against $HTLV_{IIIB}$ (Table 1). Test compound PHI-511$^R$ was also twice as active against the multidrug resistant HIV-1 strain RT-MDR (with a V106A mutation and additional mutations involving the RT residues 74V, 41L, and 215Y) than $HTLV_{IIIB}$ (Table 1). When tested against RT-MDR, PHI-511$^R$ was found to be 1,000-times more active than nevirapine, 80-times more active than delavirdine, 4-times more active than trovirdine, and as active as our previously reported fluorine-substituted thiourea compound PHI-240 (Table 1).

When tested against A17, PHI-511$^R$ was found to be 10,000-times more active than nevirapine, 5,000-times more active than delavirdine, 50-times more active than trovirdine, and 20-times more active than HI-240 (Table 1). PHI-511$^R$ was also capable of inhibiting the highly NNI-resistant HIV-1 strain A17 variant (with Y181C plus K103N mutations in RT) with an $IC_{50}$ value of 2.7 $\mu$M. In contrast, the $IC_{50}$ values of nevirapine, delavirdine, as well as trovirdine against A17 variant were >100 $\mu$M and the $IC_{50}$ value of HI-240 was 41 $\mu$M. It is noteworthy that besides PHI-511$^R$, compounds PHI-509$^R$, PHI-510$^R$, PHI-512$^R$, and PHI-513$^R$ were also more active than nevirapine, delavirdine, trovirdine, and HI-240 against the A17 variant (Table 1). These findings demonstrate that the R-isomer of halopyridyl thiourea compounds such as the $\alpha$-methyl benzyl halopyridyl compound PHI-511$^R$ have potent antiviral activity against NNI-resistant and multidrug resistant strains of HIV-1.

The invention has been described with specific chiral compounds as examples. It is expected that additional chiral compounds including carbocyclic or heterocyclic compounds of formula I fitting the NNI-RT binding pocket will function in a similar manner.

The above specification includes numerous references to patents, patent applications, and publications. Each such reference is hereby incorporated by reference for all purposes, as if fully set forth.

References
 1. Uckun, F. M., U.S. Pat. No. 5,998,411, 1999; Chem. Abstr., 1999, 131, 243185.
 2. Vig, R. et.al., Bioorg. Med. Chem. 1998, 6,1789.
 3. Vig, R. et.al., Bioorg. Med. Chem. Lett. 1998,8,1461.
 4. Mao, C. et.al., Bioorg. Med. Chem. Lett. 1998, 8, 2213.
 5. Sudbeck, E. A. et.al., Antimicro. Agents Chemother. 1998, 42, 3225.
 6. Mao, C. et.al., Bioorg. Med. Chem. Lett. 1999, 9,1593.
 7. Mao, C. et.al., Antiviral Chemistry & Chemotherapy 1999, 10, 233.
 8. Uckun, F. M. et.al., Bioorg. Med. Chem. Lett. 1999, 9,2721.
 9. Uckun, F. M. et.al., Bioorg. Med. Chem. Lett. 1999, 9, 3411.
 10. Uckun, F. M. et.al., Antivir. Chem. Chemother. 2000, 11, 135.
 11. Sudbeck, E. A. et.al., Acta. Crystallogr. 1999, C 55, 2122.

12. Atomic coordinates will be deposited in the Cambridge Structural Database, Cambridge Crystallographic Data Centre, Cambridge, U.K.

We claim:

1. A R-isomer of a compound of formula I:

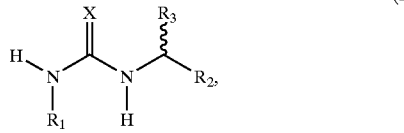

or a pharmaceutically acceptable salt thereof, wherein
X is S or O;
$R_1$ is a phenyl, pyridyl, pyrimidinyl, pyridazinyl, thiazolyl, isothiazolyl, tetrazolyl, naphthyl, imidazolyl, pyrrole, cyclohexenyl, indolyl, thienyl, piperazinyl, morpholyl, furyl, adamantyl, or piperonyl;
$R_2$ is a carbocyclic ring, and
$R_3$ is alkyl, or halo.

2. The compound of claim 1, wherein $R_1$ is pyridyl.
3. The compound of claim 1, wherein $R_1$ is halopyridyl.
4. The compound of claim 1, wherein $R_1$ is thiazolyl.
5. The compound of claim 1, wherein $R_1$ is halothiazolyl.
6. The compound of claim 1, wherein $R_2$ is a five or six-membered, saturated or unsaturated ring.
7. The compound of claim 1, wherein $R_2$ is phenyl, cyclohexyl, cyclohexenyl, or cyclopentyl.
8. The compound of claim 1, wherein $R_2$ is phenyl.
9. The compound of claim 1, wherein $R_2$ is cyclohexyl.
10. The compound of claim 1, wherein $R_3$ is halo.
11. The compound of claim 1, wherein $R_3$ is $CH_3$, $CH_3 CH_2$, or $CH(CH_3)_2$.
12. The compound of claim 1, wherein $R_3$ is $CH_3$.
13. A compound selected from:
   N-[1-(1-(1R)-cyclohexylethyl)]-N-[2-(5-bromopyridyl)]thiourea (PHI-509$^R$);
   N-[1-(1-(1R)-cyclohexylethyl)]-N-[2-(5-chloropyridyl)]thiourea (PHI-510$^R$);
   N-[1-(1-(1R)-α-methylbenzyl)]-N'-[2-(5-bromopyridyl)]thiourea (PHI511$^R$);
   N-[1-(1-(1R)-α-methylbenzyl)]-N'-[2-(5-chloropyridyl)]thiourea (PHI-512$^R$);
   N-[1(1-(1R)-cyclohexylethyl)]-N'-[2-(thiazolyl)]thiourea (PHI-513$^R$); and
   a pharmaceutically acceptable salt or ester thereof.
14. A composition comprising a compound of claim 1 and a pharmaceutically acceptable carrier.
15. A compound N-[1-(1-(1R)-cyclohexylethyl)]-N-[2-(5-bromopyridyl)]thiourea (PHI-509$^R$) or a pharmaceutically acceptable salt or ester thereof.
16. A compound N-[1-(1-(1R)-cyclohexylethyl)]-N-[2-(5-chloropyridyl)]thiourea (PHI-510$^R$) or a pharmaceutically acceptable salt or ester thereof.
17. A compound N-[1-(1-(1R)-α-methylbenzyl)]-N'-[2-(5-bromopyridyl)]thiourea (PHI-511$^R$) or a pharmaceutically acceptable salt or ester thereof.
18. A compound N-[1-(1-(1R)-α-methylbenzyl)]-N'-[2-(5-chloropyridyl)]thiourea (PHI-512$^R$) or a pharmaceutically acceptable salt or ester thereof.
19. A compound N-[1-(1-(1R)-cyclohexylethyl)]-N'-[2-(thiazolyl)]thiourea (PHI-513$^R$) or a pharmaceutically acceptable salt or ester thereof.

* * * * *